United States Patent
El-Hoiydi

(10) Patent No.: US 10,694,301 B2
(45) Date of Patent: Jun. 23, 2020

(54) AUDIO TRANSMISSION SYSTEM

(71) Applicant: SONOVA AG, Staefa (CH)

(72) Inventor: Amre El-Hoiydi, Neuchâtel (CH)

(73) Assignee: Sonova AG, Staefa (CH)

( * ) Notice: Subject to any disclaimer, the term of this patent is extended or adjusted under 35 U.S.C. 154(b) by 0 days.

(21) Appl. No.: 16/095,617

(22) PCT Filed: May 3, 2016

(86) PCT No.: PCT/EP2016/059929
§ 371 (c)(1),
(2) Date: Oct. 22, 2018

(87) PCT Pub. No.: WO2017/190773
PCT Pub. Date: Nov. 9, 2017

(65) Prior Publication Data
US 2019/0141459 A1    May 9, 2019

(51) Int. Cl.
H04R 25/00    (2006.01)
H04R 1/10    (2006.01)
(Continued)

(52) U.S. Cl.
CPC ....... *H04R 25/554* (2013.01); *A61N 1/36036* (2017.08); *H04L 45/306* (2013.01);
(Continued)

(58) Field of Classification Search
CPC .............. H04R 1/1091; H04R 2460/13; H04R 2201/107; H04R 1/083; H04R 1/406; H04R 3/005
See application file for complete search history.

(56) References Cited

U.S. PATENT DOCUMENTS 8,144,903 B2    3/2012  Haenggi et al.
8,849,202 B2    9/2014  Linde et al.
(Continued)

FOREIGN PATENT DOCUMENTS

WO    2014/086388    6/2014
WO    2015/185123    12/2015

OTHER PUBLICATIONS

Cartes, Gomez et al. (Overview andEvaluation of Bluetooth Low Energy: An Emerging Low-Power Wireless Technology, 2012 (Year: 2012).*
International Search Report and Written Opinion received in International Application No. PCT/EP16/059929, dated Feb. 16, 2017.

*Primary Examiner* — Sunita Joshi
(74) *Attorney, Agent, or Firm* — ALG Intellectual Property, LLC

(57) ABSTRACT

There is provided an audio transmission system, comprising a plurality of audio transmission units including at least a first audio transmission unit and a second audio transmission unit and at least one audio receiver unit, wherein the first audio transmission unit and the at least one audio receiver unit are configured to establish a first wireless link for transmitting audio data from the first audio transmission unit to the audio receiver unit, the first audio transmission unit and the second audio transmission unit are configured to establish a second wireless link for transmitting a link parameter set from the first audio transmission unit to the second audio transmission unit, the link parameter set allowing the second audio transmission unit to impersonate the first audio transmission unit for transmitting audio data from the second audio transmission unit via the first wireless link to the audio receiver device.

27 Claims, 2 Drawing Sheets

(51) Int. Cl.
    *H04M 1/60*         (2006.01)
    *H04R 3/00*         (2006.01)
    *A61N 1/36*         (2006.01)
    *H04L 12/725*      (2013.01)
    *H04L 12/721*      (2013.01)
    *H04W 40/00*      (2009.01)

(52) U.S. Cl.
    CPC .......... *H04L 45/66* (2013.01); *H04M 1/6066* (2013.01); *H04R 1/1091* (2013.01); *H04R 3/00* (2013.01); *H04W 40/00* (2013.01); *H04R 25/552* (2013.01); *H04R 2225/55* (2013.01); *H04R 2420/07* (2013.01); *H04R 2460/03* (2013.01)

(56) References Cited

U.S. PATENT DOCUMENTS

| | | |
|---|---|---|
| 9,131,322 B2 | 9/2015 | Solum |
| 9,247,355 B2 | 1/2016 | El-Hoiydi |
| 2005/0094795 A1* | 5/2005 | Rambo .................. H04M 9/08 379/202.01 |
| 2010/0135512 A1 | 6/2010 | Haenggi et al. |
| 2012/0058727 A1 | 3/2012 | Cook et al. |
| 2012/0314890 A1 | 12/2012 | El-Hoiydi et al. |
| 2015/0003623 A1* | 1/2015 | Rasmussen .......... G10K 11/002 381/71.6 |
| 2015/0319557 A1* | 11/2015 | El-Hoiydi ............ H04R 25/556 455/41.2 |
| 2016/0057549 A1* | 2/2016 | Marquis ................ H03G 3/344 381/315 |

\* cited by examiner

AUDIO TRANSMISSION SYSTEM

The invention relates to an audio transmission system comprising at least two audio transmission units and an audio receiver unit, with audio data being transmitted from the at least two transmission units to the receiver unit.

A multi talker network (MTN) is a system comprising a plurality of audio transmission units which are used by different persons which may speak to other persons and which may transmit their audio signals, which are typically captured by a microphone arrangement included in the audio transmission unit, via a wireless link to at least one audio receiver device, such as a hearing instrument which typically is worn at ear level. In other words, the audio transmission units typically act as wireless microphones for transmitting audio signals via a wireless link from a speaker using the audio transmission unit to a listener using the audio receiver device. Nowadays such MTN typically are implemented as systems using a digital audio link. In order to allow simple and convenient use of such system it is typically desired to implement the system based on a broadcast protocol for the wireless audio link.

U.S. Pat. No. 8,144,903 B2 relates to a MTN system using an analog or a digital audio link from a plurality of wireless microphones to a plurality of hearing aids, wherein the wireless microphone units communicate with each other via an assistive digital link in order to ensure that only one of the wireless microphone units is allowed at a time to transmit its audio signals via the audio link. The right to transmit is given to that wireless microphone unit which presently detects voice activity; in case that two or more of the wireless microphone units detect voice activity that one is awarded the right to transmit which has detected voice activity first. The microphone units are to be worn around the user's neck or on the user's belt.

U.S. Pat. No. 9,247,355 B2 relates to a MTN system comprising a plurality of audio transmission units, such as wireless microphone units, and a plurality of audio receiver units, such as hearing instruments. The wireless audio link uses a proprietary protocol based on a TDMA broadcasting scheme.

U.S. Pat. No. 9,131,322 B2 relates to hearing assistance system providing for wireless communication between hearing assistance devices which are in a Bluetooth connection with a host device, wherein during a Bluetooth connection interval one or more time slots are used for communication between the host device and one or more of the hearing assistance devices, while one or more additional time slots are reserved for communication between the hearing assistance devices.

U.S. Pat. No. 8,849,302 B2 relates to a system comprising an electronic devices, such as hearing aids, which communicate with each other via a wireless link using a Bluetooth low energy (BLE) protocol, wherein the receiving electronic device receives a data channel protocol data unit in a link layer of a BLE protocol stack; the receiving electronic device then reads a field in a header of the data channel protocol data unit to determine if the header indicates that a payload of the data channel protocol data unit contains audio data. When the header indicates that the payload of the data channel protocol data unit contains audio data, the receiving electronic device is configured to send the audio data from the payload to an audio layer in the BLE protocol stack for processing.

US 2012/0058727 A1 relates to a system comprising an audio source and two wireless loudspeakers, wherein the audio source sends an audio signal via a secondary wireless link to a first one of the loudspeakers which provides network information to a second one of the loudspeakers via a primary wireless link, wherein the network information received by the second one of the loudspeakers enables the second one of the loudspeakers to eavesdrop the secondary wireless link in order to receive audio data from the audio source.

WO 2014/086388 A1 relates to a system for wireless streaming of an audio signal from an audio source, such as a mobile phone, to a plurality of audio receiver devices, such as hearing aids, wherein a modified Bluetooth protocol is used for streaming an audio signal to two hearing aids by enabling one of the two hearing aids to eavesdrop the audio stream by use of an asynchronous connection oriented logical link (ACL) connection between the audio transmission device and the hearing aid in order to achieve synchronization of the hearing aid with the audio transmission device; the other hearing aid is connected to the audio source by a common point-to-point connection using the standard Bluetooth protocol.

WO 2015/185123 A1 relates to a method for simplified pairing of an audio source, such as a mobile phone, and two hearing assistance devices, wherein the first hearing device first pairs with the audio source and thereafter pairs a second time with the audio source, however, this time impersonating the second hearing assistance device, wherein the first hearing assistance device has received the information required for impersonating the second hearing assistance device via a communication link between the two hearing assistance devices. This communication link then is also used for transmitting the pairing information obtained by the first hearing assistance device to the second hearing assistance device.

It is an object of the invention to provide for an audio transmission system comprising a first audio transmission unit, a second audio transmission unit and an audio receiver unit, wherein both audio transmission units should be enabled in a particularly simple manner to transmit audio signals to the receiver unit. It is a further object to provide for a corresponding audio transmission method.

According to the invention these objects are achieved by a system as defined in claim 1 and a method as defined in claim 24.

The invention is beneficial in that, by transmitting a link parameter set from the first audio transmission unit to the second audio transmission unit via a second wireless link, which the link parameter set allows the second audio transmission unit to impersonate the first audio transmission unit for transmitting audio data from the second audio transmission unit via the first wireless link to the audio receiver device, with the first wireless link also being used by the first audio transmission unit for transmitting audio data to the audio receiver unit, a multipoint-to-point or multipoint-to-multipoint wireless link for audio data transmission may be implemented in a particularly simple manner. In other words, this invention allows for multiple transmitters to act as a single transmitter towards one or more receivers that implement a standard audio reception protocol that did not foresee the option to support multiple transmitters.

Preferably, the first wireless link uses the standard BLE protocol.

Preferred embodiments of the invention are defined in the dependent claims.

Hereinafter, the examples of the invention will be illustrated by reference to the attached drawings, wherein.

Figure 1:
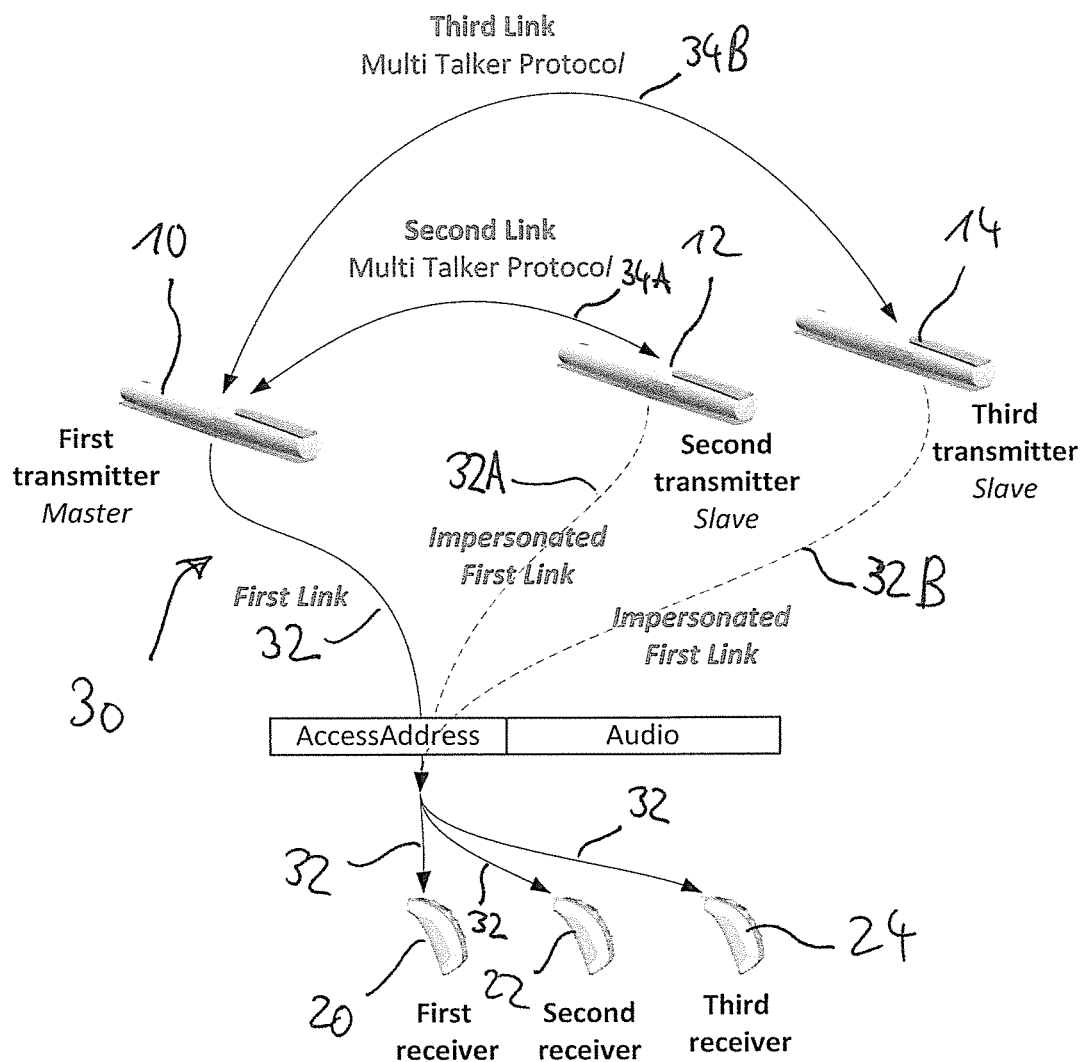
FIG. 1 is an illustration of an example of an audio transmission system according to the invention.

FIG. 1 is a schematic illustration of an example of an audio transmission system of the invention, comprising a plurality of audio transmission units 10, 12, 14 and a plurality of audio receiver units 20, 22, 24, wherein the audio transmission units 10, 12, 14 are configured to transmit audio signals via a wireless audio link 30 to the audio receiver units 20, 22, 24.

The audio transmission units, according to one example, may be implemented as wireless microphone units comprising at least one microphone for capturing audio signals from which the audio data to be transmitted to the audio receiver units is generated. In particular, the audio transmission units may be implemented as body-worn devices for capturing speech from a person wearing the respective audio transmission unit. For example, the audio transmission units may be worn around the person's neck at the chest, or they may be implemented as lapel microphones (i.e. as clip-on microphones to be worn at the person's clothes). According to another example, the audio transmission units may be configured as devices to be held in the hand of a person for capturing speech from this person or for capturing speech from another person. The audio transmission units may also comprise an interface for receiving audio data from an external audio source, such as a wireless TV set, so as to act as an audio streaming device; such audio interface may be provided alternatively or in addition to a microphone. According to another example, the transmission units may be designed as a table microphone unit to be placed on a table for capturing speech from persons sitting at the table. According to still another example, the audio transmission units may be configured to be worn at ear level for capturing speech from the person wearing the audio transmission unit, with the audio transmission unit comprising at least one ear level microphone and/or a boom microphone. It is to be understood that the system may comprise different types of such audio transmission units.

The audio receiver units typically form part of or are coupled to a hearing assistance device comprising an output transducer for stimulating a user's hearing. Typically, such hearing assistance device is to be worn at ear level. In particular, such hearing assistance device may be a hearing instrument, such as a hearing aid, or an auditory prosthesis, such as a cochlear implant, or it may be a wireless earbud or a wireless headset. According to one example, the audio receiver units may be provided in pairs, each pair forming a binaural system. It is to be understood that the plurality of audio receiver units may include different types of audio receiver units.

In the example of FIG. 1 the audio transmission units are illustrated as hand-held microphone units, and the audio receiver units are illustrated as hearing aids.

Figure 2:
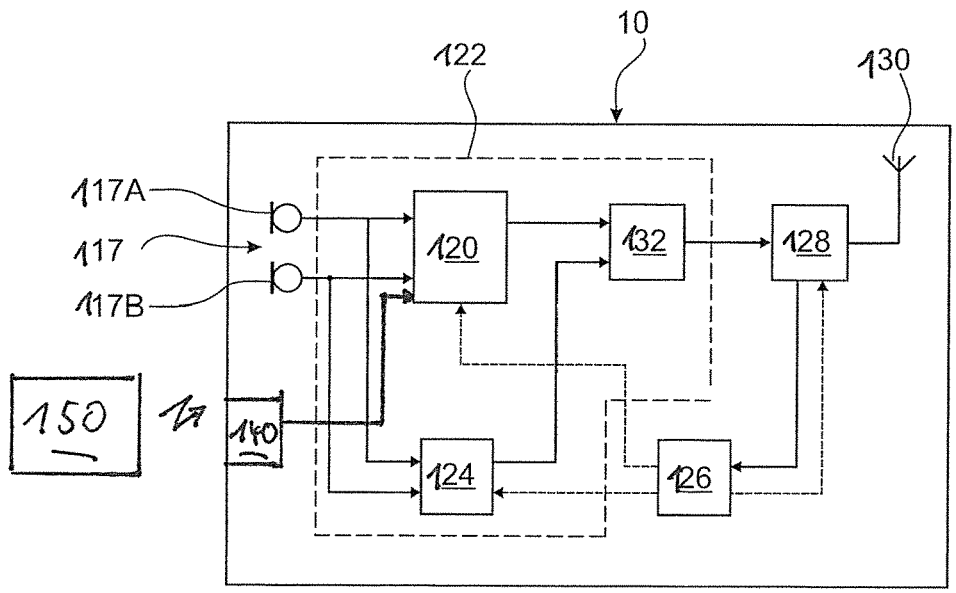
FIG. 2 shows an example of a block diagram of an audio transmission unit to be used with the invention.

FIG. 2 shows a block diagram of an example of an audio transmission unit which may be used in the invention, wherein the audio transmission unit 10 comprises a microphone arrangement 17 for capturing audio signals from a speaker's voice, an audio signal processing unit 120 for processing the captured audio signals, a digital transmitter 128 and an antenna 130 for transmitting the processed audio signals as an audio stream consisting of audio data via the wireless link 30 to the audio receiver units. Typically, the audio transmission unit 10 comprises additional components such as a voice activity detector (VAD) 124, which may be implemented, together with the audio signal processing unit 120, by a digital signal processor (DSP) 122. In addition, the audio transmission unit 10 also may comprise a microcontroller 126 acting on the DSP 122 and the transmitter 128. Typically, the microphone arrangement 117 comprises at least two spaced-apart microphones 117A, 117B, the audio signals of which may be used in the audio signal processing unit 120 for acoustic beamforming in order to provide the microphone arrangement 117 with a directional characteristic.

The VAD 124 uses the audio signals from the microphone arrangement 117 as an input in order to determine the times when the person using the audio transmission unit 10 is speaking, i.e. the VAD 124 determines whether there is a speech signal having a level above speech level threshold value. The VAD 124 may also analyze the audio signal in order to determine the signal to noise ratio (SNR) of the captured audio signal in order to determine whether it is above an SNR threshold value. An appropriate output signal of the VAD 124 may be transmitted via the wireless interface 128, 130, together with the audio data provided by the audio signal processing unit 120. To this end, a unit 132 may be provided which serves to generate a digital signal merging an audio signal from the processing unit 120 and data generated by the VAD 124, which digital signal is supplied to the transmitter 128.

The audio transmission unit 10 may also comprise an interface 140 (wired or wireless) for receiving audio data from an external audio source 150, such as TV set or a mobile phone.

Figure 3:
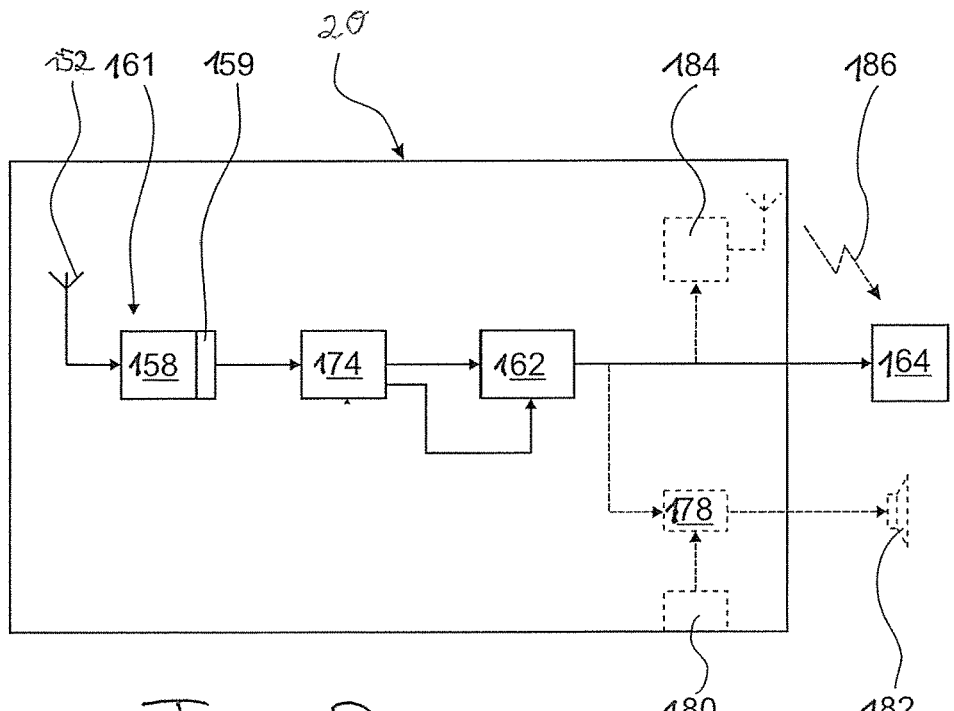
FIG. 3 shows a block diagram of an audio receiver unit to be used with the invention.

In FIG. 3 an example of a block diagram of an audio receiver unit to be used with the invention is shown, wherein the audio receiver unit 20 comprises an antenna 152 connected to a digital transceiver 161 including a demodulator 158 and a buffer 159. The signals received by the antenna 152 are demodulated in the transceiver 161, and the demodulated signals are supplied via the buffer 159 to a DSP 174 acting as a signal processing unit which separates the signals into audio signals and control data and which is provided for advanced processing, e.g. gain control, of the audio signals according to the information provided by the control data. The processed audio signals, after digital-to-analog conversion, are supplied to a variable gain amplifier 162 which serves to amplify the audio signals by applying a gain controlled by the control data received by the transceiver 161. The amplified audio signals may be then supplied to a hearing aid 164. Alternatively, the receiver unit 20 may include a power amplifier 178 which may be controlled by manual volume control 180 and which supplies power amplified audio signals to a loudspeaker 182 which may be an ear-worn element integrated within in or connected to the receiver unit 20. According to another alternative, the receiver unit 20 may be integrated within a hearing aid. A further alternative implementation of the receiver unit 20 is a neck-worn device having a transmitter 184 for transmitting the received signals via a magnetic induction link 186 to a hearing aid 164. A further alternative implementation of the receiver unit 20 is a neck-worn device having an analog audio electrical interface for transmitting the received signals electrically to a headphone.

The wireless links of the system of FIG. 1 are configured such that a MTN is implemented wherein each audio transmission unit may transmit its audio signals via a wireless link to each of the audio receiver units, thereby implementing a multipoint-to-multipoint link. While such multipoint-to-multipoint links may be implemented using a proprietary network protocol (see, for example, U.S. Pat. No. 9,247,355 B2 as discussed above), standard wireless communication protocols such as BLE, often only provide for point-to-point links. Even if such standard protocol were extended to allow broadcasting of audio data, as mentioned in U.S. 8,849,202 B2, such point-to-multipoint link would not lead to the desired multipoint-to-multipoint link.

As illustrated in FIG. 1, such extension of a point-to-multipoint to a multipoint-to-multipoint (or an extension of a point-to-point link to a multipoint-to-multipoint link) can be implemented as follows: one of the audio transmission units, such as the first audio transmission unit 10, establishes a first wireless link 32 with at least one of the audio receiver units 20, 22, 24 (typically, as illustrated in FIG. 1, the first link 32 is implemented as an audio broadcast link; however, in principle it also could be a point-to-point link with only one audio receiver unit). The first link 32 then may be used by the first audio transmission unit 10 to transmit audio data to the audio receiver units 20, 22, 24. Thus, the first audio transmission unit 10 is aware of all information required for audio data transmission via the first link 32 (hereinafter, such information will be referred to as "link parameter set").

In addition, the first audio transmission unit 10 communicates with the other audio transmission units, i.e. with the second audio transmission unit 12 and the third audio transmission unit 14, via a second wireless link 34A and a third wireless link 34B, respectively, wherein the second and third link 34A, 34B may use a protocol which is different from the protocol of the first link 32, but they also may use the same protocol as the first link 32. Typically, the second and third link 34A, 34B are configured to implement a master-slave architecture, wherein the first transmission unit 10 acts as the master and the second and third audio transmission unit 12, 14 act as slaves.

The first audio transmission unit 10 may use the second and third link 34A, 34B for communicating the link parameter set required for transmitting audio data via the first link 32 to the second and third audio transmission unit 12, 14, whereupon the second and third audio transmission unit 12, 14 are enabled to impersonate the first audio transmission unit 10 for transmitting audio data from the second and third transmission unit 12, 14 to the audio receiver units 20, 22, 24, thereby creating an impersonated first link 32A from the second audio transmission unit 12 to the audio receiver units 20, 22, 24 and an impersonated first link 32B from the third audio transmission unit 14 to the audio receiver unit 20, 22, 24, respectively.

It is understood that the audio data may be composed of a compressed audio signal and of audio related control data, related for example to the gain to be applied to the signal, to the surrounding noise measured at the audio transmission unit or to the state of voice activity as detected by the VAD 124.

The second and third link 34A, 34B may also be configured to implement a one way broadcast architecture (e.g. using BLE advertising), wherein the first transmission unit 10 broadcasts the "link parameter set" to the second audio transmission unit 12 and to the third audio transmission unit 14.

The second and third link 34A, 34B may also be used by the second audio transmission unit 12 and third audio transmission unit 14 to transmit information relevant for the first link 32 to the first audio transmission unit 10. For example, such information could be the value of a packet counter, or the list of good channels to use in an adaptive hopping scheme. It is to be understood that the master roles may be swapped among transmitters after the initial distribution of the "link parameter set".

By enabling the second and third audio transmission unit 12, 14 to impersonate the first audio transmission unit 10, the first, second and third audio transmission unit 10, 12, 14 appear, when seen from the view of the audio receiver units 20, 22, 24, as a single audio transmission unit, thereby extending the first link 32 which is actually established between the first audio transmission unit 10 and the audio receiver unit 20, 22, 24 to the second and third transmission unit 12, 14; so as to implement a multipoint-to-multipoint connection.

Preferably, the protocol used by the first link 32 is the standard BLE protocol. The use of such standard protocol typically requires knowledge of the access address, timing synchronization information and frequency hopping sequence information in order to be able to impersonate the first audio transmission unit 10 for using the first link 32. Typically, the access address is selected by the first audio transmission unit 10 when establishing the first link 32. Consequently, in this case the link parameter set communicated by the first audio transmission 10 to the second and third audio transmission unit 12, 14 includes at least these parameters, i.e. access address, timing synchronization information and frequency hopping sequence information. In addition, the linked parameter set may include a decryption key which may be required for decrypting encrypted data.

The second and third link 34A, 34B may use a standard protocol, such as BLE protocol, or it may use a proprietary protocol.

The term "to impersonate" or "impersonation", which is also used in cryptography, is generally to be understood in the sense of "to pretend to be (another person)" or "to assume or act the character of".

The invention claimed is:

1. An audio transmission system, comprising a plurality of audio transmission units including at least a first audio transmission unit and a second audio transmission unit and an audio receiver unit, wherein
the first audio transmission unit and the audio receiver unit are configured to establish a first wireless link for transmitting audio data from the first audio transmission unit to the audio receiver unit,
the first audio transmission unit and the second audio transmission unit are configured to establish a second wireless link for transmitting a link parameter set from the first audio transmission unit to the second audio transmission unit, the link parameter set including parameters used to establish the first wireless link,
the second audio transmission unit configured to
use the link parameter set to establish an impersonated first wireless link between the second audio transmission unit and the audio receiver unit and that uses the parameters included in the link parameter set, and
transmit additional audio data directly to the audio receiver unit via the impersonated first wireless link;
wherein the link parameter set is configured to cause the first and second audio transmission units to appear, from a view of the audio receiver unit, as a single audio transmission unit.

2. The system of claim 1, wherein the first wireless link uses a standard protocol.

3. The system of claim 2, wherein the first wireless link uses the standard Bluetooth Low Energy protocol.

4. The system of claim 1, wherein the link parameter set comprises at least one of the access address used by the first audio transmission unit, timing synchronization information, frequency hopping sequence information and a decryption key.

5. The system of claim 1, wherein the second wireless link uses a standard protocol.

6. The system of claim 5, wherein the second wireless link uses the Bluetooth Low Energy protocol.

7. The system of claim 1, wherein the second wireless link uses a proprietary protocol.

8. The system of claim 1, wherein the second wireless link is configured to implement a master slave architecture, wherein the first audio transmission unit acts as a master and the second audio transmission unit acts as a slave.

9. The system of claim 1, wherein the plurality of transmission units comprises at least one additional audio transmission unit, wherein the first audio transmission unit and each additional audio transmission unit are configured to establish an additional wireless link for transmitting the link parameter set from the first audio transmission unit to the additional audio transmission unit, the link parameter set allowing the additional audio transmission unit to impersonate the first audio transmission unit for transmitting audio data from the additional audio transmission unit via an additional impersonated first wireless link to the audio receiver unit.

10. The system of claim 9, wherein each additional wireless link uses the same scheme as the second wireless link.

11. The system of claim 1, wherein at least one of the audio transmission units comprises at least one microphone for capturing audio signals to generate the audio data.

12. The system of claim 1, wherein at least one of the audio transmission units is a body-worn device for capturing speech from a person wearing the respective audio transmission unit.

13. The system of claim 12, wherein said at least one of the audio transmission units is configured to be worn around the person's neck at the chest, at the person's clothes as a lapel microphone, or at the person's belt.

14. The system of claim 12, wherein said at least one of the audio transmission units is configured to be worn at ear level and comprise an ear level microphone or a boom microphone.

15. The system of claim 1, wherein at least one of the audio transmission units comprise an interface for receiving audio data from an external audio source.

16. The system of claim 1, wherein at least one of the audio transmission units is configured to be held in the hand of a person for capturing speech from this person or from another person.

17. The system of claim 1, wherein at least one of the audio transmission units is configured to be placed on a table for capturing speech from persons located at the table.

18. The system of claim 1, wherein the system comprises an additional audio receiver unit.

19. The system of claim 1, wherein the audio receiver unit forms part of or is coupled to a hearing assistance device comprising an output transducer for stimulating a user's hearing.

20. The system of claim 19, wherein the hearing assistance device is configured to be neck-worn and comprises a transmitter for transmitting the received signals via a magnetic induction link to a hearing aid.

21. The system of claim 19, wherein the hearing assistance device is configured to be a neck-worn device having an analog audio electrical interface for transmitting the received signals electrically to a headphone.

22. The system of claim 19, wherein the hearing assistance device is configured to be worn at ear level.

23. The system of claim 22, wherein the hearing assistance device is a hearing instrument or an auditory prosthesis.

24. A method for audio data transmission, comprising
establishing a first wireless link between a first audio transmission unit and an audio receiver unit for transmitting audio data from the first audio transmission unit to the audio receiver unit,
establishing a second wireless link between the first audio transmission unit and a second audio transmission unit and transmitting a link parameter set from the first audio transmission unit to the second audio transmission unit via the second wireless link, the link parameter set including parameters used to establish the first wireless link,
using, by the second audio transmission unit, the link parameter set to
establish an impersonated first wireless link between the second audio transmission unit and the audio receiver unit and that uses the parameters included in the link parameter set, and
transmit additional audio data directly to the audio receiver unit via the impersonated first wireless link;
wherein the link parameter set is configured to cause the first and second audio transmission units to appear, from a view of the audio receiver unit, as a single audio transmission unit.

25. The method of claim 24, wherein the second wireless link is used to assign a master role to the first audio transmission unit and to assign a slave role to the second audio transmission unit.

26. The method of claim 24, wherein the first audio transmission device chooses an access address and starts transmission of audio data via the first wireless link, wherein the first audio transmission device then transmits the link parameter set, including the access address chosen by the first transmission device, via the second wireless link to the second audio transmission unit.

27. The method of claim 26, wherein the link parameter set includes timing synchronization information and frequency hopping sequence information.

* * * * *